United States Patent

Cully et al.

[11] Patent Number: 5,342,633
[45] Date of Patent: Aug. 30, 1994

[54] PROCESS FOR THE PRODUCTION OF EGG YOLK WITH REDUCED CHOLESTEROL CONTENT

[75] Inventors: Jan Cully, Garching; Heinz-Rüdiger Vollbrecht, Altenmarkt, both of Fed. Rep. of Germany

[73] Assignee: SKW Trostberg Aktiengesellschaft, Trostberg, Fed. Rep. of Germany

[21] Appl. No.: 120,309

[22] Filed: Sep. 13, 1993

Related U.S. Application Data

[63] Continuation of Ser. No. 755,489, Sep. 5, 1991, abandoned.

[30] Foreign Application Priority Data

Sep. 14, 1990 [DE] Fed. Rep. of Germany ....... 4029287

[51] Int. Cl.$^5$ ............................ A23J 3/00; A23L 1/32
[52] U.S. Cl. ....................................... 426/47; 426/490; 426/614
[58] Field of Search ................. 426/47, 417, 442, 490, 426/491, 614, 7, 47, 61, 64, 492, 494, 495, 478

[56] References Cited

U.S. PATENT DOCUMENTS

| | | |
|---|---|---|
| 3,491,132 | 1/1970 | Reiners et al. |
| 4,383,992 | 5/1983 | Lipari et al. |
| 4,650,757 | 3/1987 | David et al. ........................... 426/52 |
| 4,880,573 | 11/1989 | Courregelongue et al. ......... 426/417 |
| 4,980,180 | 12/1990 | Cully et al. ............................ 426/614 |
| 5,063,077 | 11/1991 | Vollbrecht et al. .................. 426/614 |

FOREIGN PATENT DOCUMENTS

| | | |
|---|---|---|
| 326469 | 8/1989 | European Pat. Off. |
| 327098 | 8/1989 | European Pat. Off. |
| 350379 | 1/1990 | European Pat. Off. |

OTHER PUBLICATIONS

Chemical Abstracts vol. 101, p. 256, left hand column, Item No. 2898B.

Data Base WPIL/Derwent AN=87-296033 [42] DW8742.
Data Base WPI/Derwent AN=76-19971X [11] DW7611.
R. W. Burley and H. W. Cook "Isolation and Composition of Avian Egg Yolk Granules and Their Constituent—And—Lipovitellins", Can. J. Biochem. Physiol. vol. 39 (1961) pp. 1295–1307.
D. V. Vadehra, Joan M. Bian and R. W. Burley, "Lipid–Protein Globules of Avian Egg Yolk. Isolation and Properties of Glubules Stable in Concentrated Sodium Chloride Solution", Biochem. J. (1977) 166, 619–624.
R. W. Burley "Studies on the Apoproteins of the Major Lipoprotein of the Yolk of Hen's Eggs. III. Influence of Salt Concentration During Isolation on the Amount and Composition of the Apoproteins", Aust. J. Biol. Sci. 1978 31, 587–92.

Primary Examiner—Donald E. Czaja
Assistant Examiner—Leslie Wong
Attorney, Agent, or Firm—Felfe & Lynch

[57] ABSTRACT

A process for the production of egg yolk with a reduced cholesterol content, wherein a) the egg yolk is diluted by the addition of water or of an aqueous salt solution,
b) cholesterol and cholesterol esters which are contained in the diluted egg yolk are selectively complexed with $\beta$-cyclodextrin,
c) the $\beta$-cyclodextrin loaded with cholesterol and/or cholesterol esters are separated from the diluted egg yolk,
d) the added water is removed from the egg yolk,
e) the residual amounts of $\beta$-cyclodextrin present in the egg yolk are decomposed enzymatically with the help of $\alpha$-amylase and/or, and
f) the $\beta$-cyclodextrin is recovered by treatment with water and/or an alcohol from the $\beta$-cyclodextrin complexes and optionally returned to step b).

28 Claims, No Drawings

PROCESS FOR THE PRODUCTION OF EGG YOLK WITH REDUCED CHOLESTEROL CONTENT

This application is a continuation of application Ser. No. 07/755,489 filed Sep. 5, 1991, now abandoned.

FIELD OF THE INVENTION

The present invention is concerned with a multi-step process for the production of egg yolk with a reduced cholesterol content.

BACKGROUND OF THE INVENTION

Cholesterol and cholesterol esters are lipophilic substances which occur in numerous important foodstuffs of animal origin, for example egg yolk, meat, animal fats and the like.

Increased cholesterol values in human blood serum are regarded as being a risk factor for arteriosclerosis and for coronary heart-disease.

By means of a reduction of the intake of cholesterol, in many pathological cases it is possible again to achieve the normal cholesterol values in blood serum. For this reason, the endeavor of the foodstuff industry is to carry out a distinct reduction of the amount of cholesterol and of cholesterol esters in fat-rich foodstuffs of animal origin.

It is thereby an important problem substantially to maintain the sensory and nutrition-physiological properties of the foodstuffs.

Admittedly, a number of processes ere already known fop the separation of cholesterol and cholesterol esters but, because of chemical changes of important components of the starting material, for example of proteins, triglycerides and the like, many of these methods are not suitable for reducing the cholesterol content of foodstuffs.

A relatively gentle process, which has become known only recently, makes use of carbon dioxide high pressure extraction for the removal of cholesterol and of cholesterol esters (cf. V. Krukonis, Supercritical Fluid Processing, International Symposium on Supercritical Fluids, Nice, 1988).

This process is admittedly characterized by the physiological harmlessness of the extraction agent (carbon dioxide) but working at a high pressure is technically rather expensive. Furthermore, under gentle conditions, cholesterol and cholesterol esters cannot be selectively removed therewith because triglycerides are also co-extracted. An improvement of the selectivity by increasing the temperature is admittedly in principle possible but this has a negative effect on the loading of the carbon dioxide with cholesterol and cholesterol esters and on the quality of the product obtained.

From EP-A 0,326,469, it is known to remove cholesterol derivatives from egg yolk with the help of β-cyclodextrin, but in process, the long loading times and the comparatively small reduction of the cholesterol content in the egg yolk is disadvantageous.

OBJECT OF THE INVENTION

Therefore, it is an object of the present invention to provide a process for the removal of cholesterol and/or of cholesterol esters from egg yolk which does not suffer from the disadvantages of the prior art but rather, with low technical expense and under gentle conditions, makes possible a substantially selective reduction of the content of these substances.

DESCRIPTION OF THE INVENTION

Thus, according to the present invention, there is provided a process for the production of egg yolk with a reduced cholesterol content, wherein
 a) the egg yolk is diluted by the addition of water or of an aqueous salt solution,
 b) cholesterol and cholesterol esters which are contained in the diluted egg yolk are selectively complexed with β-cyclodextrin,
 c) the β-cyclodextrin loaded with cholesterol and/or cholesterol esters is separated from the diluted egg yolk,
 d) the added water is removed from the egg yolk,
 e) the remaining amounts of β-cyclodextrin present in the egg yolk are decomposed with the help of α-amylase and/or CTGase enzymatically and
 f) the β-cyclodextrin is recovered from the β-cyclodextrin complexes by treatment with water and/or an alcohol and optionally returned to process step b).

Surprisingly, we have found that in this way egg yolk products are obtained with a low total cholesterol content and with good sensory properties. Furthermore, practically no β-cyclodextrin is present in the cholesterol-reduced egg yolk thus obtained. It was also not foreseeable that this would happen.

In the process according to the present invention, in step a) the egg yolk is diluted by the addition of water or of an aqueous salt solution. The amount of water can vary within wide limits, but for economic reasons it has proved to be advantageous to use 10 to 400% and preferably 100 to 300% by weight of water, referred to the initial weight of the egg yolk. Due to this addition of water, the granule fraction precipitates out as a solid and can be separated very simply from the liquid egg yolk plasma by conventional solid/liquid separation methods, for example by centrifuging. In that case, in the further process, egg yolk plasma is used instead of egg yolk.

Instead of water, an aqueous salt solution can also be added to the egg yolk. In the case of this embodiment, a separation of the egg yolk emulsion into granula fraction and egg yolk plasma is prevented. As a salt solution, there is preferably used a 5 to 20% solution of sodium chloride or a 1 to 10% solution of ammonium hydrogen carbonate in order to achieve the desired degree of dilution.

In the following step b) of the process according to the present invention, there then takes place the removal of the cholesterol and of the cholesterol derivatives from the diluted egg yolk or egg yolk plasma by complexing with β-cyclodextrin, which makes possible an especially selective binding of the cholesterols.

The amount of β-cyclodextrin can be varied within wide limits, but it is preferred to use 3 to 40% by weight of β-cyclodextrin, referred to the dry weight of the egg yolk.

By virtue of this complexing with β-cyclodextrin, which can take place according to known methods, for example by simple mixing or stirring, there are removed, depending upon the amount of β-cyclodextrin added, about 60 to 99% of the cholesterol and of the cholesterol esters, whereas the other components of the egg yolk remain substantially in the liquid phase. Due to the previous dilution of the egg yolk with water, it is also possible to carry out the removal of the cholesterol with β-cyclodextrin at comparatively low temperatures from 4° to 20° C. very gently and completely. Especially preferably the complexing takes place by stirring the mixture at 4° to 10° C.

In step c) of the process according to the present invention, the β-cyclodextrin loaded with cholesterol and/or cholesterol esters is separated from the liquid egg yolk phase. In principle, the conventional processes and methods for the separation of solid materials and liquids can be used. Because of the rapid and complete separation, according to the present invention it is preferred to use centrifuging. Other separation processes, for example filtration, are also well suited.

After separation of the β-cyclodextrin complexes, the added salts can be removed from the egg yolk by known methods if the presence of these salts is undesired for the intended purpose of use. In the case of ammonium hydrogen carbonate, the removal can be carried out very simply by allowing this compound to vaporize by heating the egg yolk mixture to 40° to 80° C. The vaporization is preferably carried out in a vacuum at a temperature of from 55° to 70° C. If it is desired to remove sodium chloride from the age yolk, this is preferably accomplished by dialysis, electrodialysis, cross-flow ultrafiltration or other known methods.

After separation of the β-cyclodextrin complexes from the substantially cholesterol-free, diluted egg yolk or egg yolk plamsa, and optionally after removal of the salts, the egg yolk or egg yolk plasma is concentrated in step d) to such an extent that it again reaches the original solid material content. This step can be carried out very gently and without problems with conventional methods, for example vacuum evaporation or membrane technology.

In step e) of the process according to the present invention, the residual amounts of β-cyclodextrin present in the egg yolk, which are usually 0.1 to 1.0% by weight, are broken down enzymatically with the help of α-amylase and/or CTGase. For this purpose α-amylases selected from the α-amylases formed by the microorganisms of the group *Aspergillus niger, Aspergillus oryzae, Bacillus polymyxa,* domestic hog pancreatic amylase, *Bacillus coagulans* and Flavobacterium, as well as α-amylases derived therefrom are preferably used. From the group of the CTGases (cyclodextrin transglycosylases =E.C. 2.4.1.19), those are especially preferred which are produced by bacteria of the Bacillus (for example *Bacillus macetans, Bacillus megaterium, Bacillus stesrothermophilus, Bacillus circulsns* and *Bacillus ohbensis,* Klebsiella (for example pneumoniae), Micrococcus (for example varians) and alkalophilic bacteria (for example No. 38-2 and 17-1), as well as CTGases derived therefrom. These α-amylases and CTGases make possible a practically complete breakdown of β-cyclodextrin. Before the addition of the enzymes to the egg yolk, it is recommended to adjust the pH of the egg yolk to the particular pH optimum of the enzyme, which can take place, for example, with the acids which are usually suitable for foodstuffs, for example citric acid. The necessary amount of enzyme depends essentially upon the initial content of β-cyclodextrin in the eggs yolk and, in the case of α-amylase, is, as a rule, 10 to 500 FAU per g of β-cyclodextrin to be removed (1 FAU=fungal α-amylase unit breaks down, under standard conditions, 5.26 g of starch in 1 hour; substrate: soluble starch, incubation time 7 to 20 minutes, temperature 37° C. pH 4.7). In the case of the CTGases, these are preferably used in an amount of 0.5 to 20 U per g of β-cyclodextrin to be removed (1 unit=- conversion of 1 μmol of substrate per minute). It is also possible to work with larger amounts of enzyme but these quickly become uneconomical because no better action is connected therewith. The treatment conditions, such as temperature and period of time, can be varied within wide limits, but temperatures from 5° to 65° C. have proved to be especially advantageous, in which case treatment times from 0.5 to 50 hours are usual. According to a preferred embodiment of the process according to the present invention, mixtures of α-amylase and CTGase are used.

It is also possible to carry out the enzymatic breakdown of the β-cyclodextrin in the diluted egg yolk phase, i.e. before the concentration step, by reversing the sequence of steps d) and e). However, this is not preferred.

After the enzyme treatment, in the case the cholesterol removal has been carried out in the egg yolk, the separated granula fraction can be resuspended in the egg yolk plasma.

Depending upon the intended purpose of use, the practically cholesterol-free egg yolk can then be further worked up. Thus, for example, it is possible to add to the egg yolk an appropriate amount of albumen in order to produce a cholesterol-reduced whole egg product.

In step f) of the process according to the present invention, the β-cyclodextrin complexed with cholesterol and/or cholesterol esters is optionally purified and then regenerated. This optional purification step is carried out by washing with water or with an aqueous salt solution, for example a solution of sodium chloride or ammonium hydrogen carbonate. The amount of water added can be varied within relatively wide limits. However, as a rule, an equal fivefold amount, referred to the weight of the β-cyclodextrin complex, suffices in order to achieve a sufficient separation of the β-cyclodextrin complexes from possible impurities, for example proteins. According to a preferred embodiment, the β-cyclodextrincholesterol complex is stirred with an equal twofold amount of water and the solid material, i.e. β-cyclodextrin complex, separated, for example by centrifuging. The essentially protein-containing water can optionally be used again for diluting the egg yolk in step a).

Subsequent to the optional washing step, the cyclodextrin complexes are treated with water and/or alcohol, whereby the β-cyclodextrin is freed from cholesterol and/or cholesterol derivatives, as well as from possibly entrained fats. The temperature of the water or alcohol is preferably from 40° to 100° C. in order to destabilize the β-cyclodextrin complexes and, at the same time, to dissolve the liberated β-cyclodextrin in the water. An alkanol containing 1 to 4 carbon atoms preferably can be used as the alcohol.

The fat-cholesterol mixture obtained in this way can, possibly after recovery of the alcohol, be used directly as a raw material in the cosmetics industry or can be further worked up for recovering the cholesterol.

The β-cyclodextrin purified with water or alcohol, possibly in several steps, is preferably dissolved in water and again used in the form of an aqueous solution or, after evaporation of the water, in the form of a powder for the complexing of the cholesterol derivatives in step b).

This recovery or recycling of the β-cyclodextrin represents a considerable economic advantage of the process according to the present invention. Furthermore, there is obtained an egg yolk with a total cholesterol content reduced by about 80 to 95%, as well as with a residual content of β-cyclodextrin of <20 ppm. Because of this good reduction of the content of cholesterol and of β-cyclodextrin, combined with the further advantages, such as low technical expense and good sensory quality of the egg yolk products obtained, the process according to the present invention is especially well suited for carrying out on a large scale.

The following Examples are given for the purpose of illustrating the present invention:

EXAMPLE 1

2 kg of egg yolk (dry weight 950 g) with a cholesterol content of 1.2% were mixed with 2 kg of an aqueous 10% by weight solution of sodium chloride.

Subsequently, the egg yolk-salt mixture was mixed with 280 g β-cyclodextrin and stirred for 60 minutes at 5° C. Thereafter, the loaded β-cyclodextrin was separated from the egg yolk phase by centrifuging.

The diluted egg yolk phase was thereupon subjected to a cross-flow ultrafiltration, the content of moisture thereby being adjusted to the original value and the content of sodium chloride being approximately halved. In the next step, the sodium chloride content was lowered to about 0.3% by weight by electrodialysis.

Subsequently, the egg yolk was incubated for 45 minutes at pH 5.5 and a temperature of 50° C. with the enzyme preparation Fungamyl 800 (1000 FAU/kg of material), the content of β-cyclodextrin thereby being reduced from about 0.5% to <20 ppm.

As product, there was obtained an egg yolk with a total cholesterol content of 0.12%, which corresponds to a 90% reduction in comparison with the untreated egg yolk.

350 g of the separated β-cyclodextrin-cholesterol complex, including entrained fats and proteins, were mixed with 400 ml of water end the solid material was separated from the liquid phase by centrifuging. The protein-containing aqueous solution was again used for diluting the egg yolk. The β-cyclodextrin-cholesterol complex separated as solid material was washed with a ninefold amount of 98% ethanol in several steps. Subsequently, the ethanolic phase was separated from solid β-cyclodextrin by centrifuging. The β-cyclodextrin was thereupon dissolved in hot water and freed from insoluble components by filtration. From this solution were subsequently obtained 198 g of pure β-cyclodextrin which was used again in the cholesterol complexing.

EXAMPLE 2

2 kg of egg yolk (dry weight 950 g), with a cholesterol content of 1.2%, were mixed with 2 kg of a 4% by weight aqueous solution of ammonium hydrogen carbonate.

Subsequently, the egg yolk-salt mixture was mixed with 300 g β-cyclodextrin and stirred for 50 minutes at 5° C. Thereafter, the loaded β-cyclodextrin was centrifuged off from the egg yolk phase.

The diluted egg yolk phase was subsequently concentrated in a vacuum at 65° C., the ammonium hydrogen carbonate thereby being removed and the moisture content adjusted to the original value.

Finally, the pH value of the egg yolk was adjusted with citric acid to 6.0 and mixed with the enzyme preparation Fungamyl 800 (300 FAU/kg of material). After incubating for 45 minutes at 50° C. 50 U of a CTGase (E.C. 2.4.1.19) from Bacillus macetans were added thereto and incubation was continued for a further 45 minutes at 50° C.

As product, there was obtained an egg yolk with a total cholesterol content of 0.1%, which corresponds to a 92% reduction in comparison with the untreated egg yolk. No residual amounts of β-cyclodextrin could be detected in the product (detection limit 20 ppm).

350 g of the separated β-cyclodextrin-cholesterol complex, including entrained fats and proteins, were mixed with 3800 g of water and boiled for 30 minutes. Subsequently, this solution was freed from undissolved components by filtration. Thereafter, 205 g of pure β-cyclodextrin were obtained from this solution which was used again for the cholesterol complexing.

EXAMPLE 3

2 kg of egg yolk (dry weight 950 g), with a total cholesterol content of 1.2%, were mixed with distilled water in a weight ratio of 1:3 and centrifuged for 15 minutes at 4° C.

6.3 kg of the so-obtained supernatant plasma fraction were decanted from the granula fraction and intimately mixed by stirring with 238 g β-cyclodextrin for 60 minutes at 4° C. Thereafter, the loaded β-cyclodextrin was separated off from the liquid plasma phase by centrifuging.

The plasma phase was incubated at a pH of 5.5 and a temperature of 50° C. for 120 minutes with a mixture of Fungamyl 800 (400 FAU/kg of material) and of a CTGase from Bacillus macetans (10 U/kg of starting material).

The plasma fraction treated in this manner was thereupon subjected to a vacuum evaporation at 50° C., the degree of moisture thereby being adjusted to the original value. The separated granula fraction was resuspended in the concentrated egg yolk plasma and the whole amount mixed with albumen in a ratio of 1:2. As product, there is obtained a whole egg with a cholesterol content of 0.07%.

350 g of the separated β-cyclodextrin complex were mixed with 700 g of water and solid material freed by centrifuging from water-soluble impurities, for example proteins. The β-cyclodextrin complex was subsequently boiled for 60 minutes three times with 900 g. of ethanol. The solid material separated by filtration was dissolved in boiling water, freed from insoluble residues by filtration, and the β-cyclodextrin solution obtained was evaporated and subjected to crystallization, 160 g of pure β-cyclodextrin thereby being recovered.

We claim:

1. In the method of reducing the cholesterol content of egg yolk, wherein the egg yolk is admixed with water whereby the egg yolk emulsion separates into a liquid plasma phase and a solid granula phase, the plasma phase is separated from the granula phase, cholesterol and cholesterol esters contained in the liquid plasma phase are selectively complexed with β-cyclodextrin, the complexed β-cyclodextrin is separated from the liquid plasma phase, the water is removed from the liquid plasma phase, and residual β-cyclodextrin present in the plasma phase is enzymatically decomposed, the improvement which comprises recovering the β-cyclodextrin by treatment of the complexed β-cyclodextrin with water, with an alcohol or with a mixture of water and an alcohol, recombining the solid granula phase with the treated liquid plasma phase and recycling the recovered β-cyclodextrin into the process for further selectively complexing cholesterol and cholesterol esters contained in the liquid plasma phase.

2. The method of claim 1, wherein 10 to 400% by weight of water, based on the starting weight of the egg yolk, are added to the egg yolk.

3. The method of claim 2, wherein 100 to 300% by weight of water, based on the starting weight of the egg yolk, are added to the egg yolk.

4. The method of claim 1, wherein the plasma phase is separated from the granula phase by centrifuging.

5. The method of claim 1, wherein 3 to 40% by weight of β-cyclodextrin, based on the dry weight of the egg yolk, are added to the separated plasma phase.

6. The method of claim 1, wherein the β-cyclodextrin is recovered by treatment of the complexed β-cyclodextrin with an equal to fivefold amount of water, alcohol or water-alcohol mixture, based on the weight of complexed β-cyclodextrin.

7. The method of claim 1, wherein the treatment of the complexed β-cyclodextrin with water, alcohol or a water-alcohol mixture is carried out at a temperature from 40° to 100° C.

8. The method of claim 6, wherein the treatment of the complexed β-cyclodextrin with an alcohol is carried out in several steps.

9. The method of claim 8, wherein the alcohol is ethanol.

10. The method of claim 1, wherein water is removed from the liquid plasma phase by vacuum distillation.

11. The method of claim 1, wherein the residual amount of β-cyclodextrin present in the plasma phase is enzymatically decomposed with domestic hog pancreatic amylase or an α-amylase formed by a microorganism selected from the group consisting of *Aspergillus niger, Aspergillus oryzae, Bacillus polymyxa, Bacillus coagulans* and Flavobacterium.

12. The method of claim 11, wherein the β-cyclodextrin is enzymatically decomposed with 10 to 500 FAU per gram of β-cyclodextrin to be decomposed.

13. The method of claim 1, wherein the residual amount of β-cyclodextrin present in the plasma phase is enzymatically decomposed with a CTGase derived from or formed by a bacteria selected from the group consisting of Bacillus, Klebsiella, Micrococcus and alkalophilic bacteria.

14. The method of claim 13, wherein the β-cyclodextrin is enzymatically decomposed with 0.5 to 20 U per gram of β-cyclodextrin to be decomposed.

15. The method of claim 1, wherein the enzymatic decomposition of β-cyclodextrin is carried out at a temperature of 5° to 65° C.

16. In the method of reducing the cholesterol content of egg yolk, wherein the egg yolk is diluted with an aqueous salt solution, cholesterol and cholesterol esters contained in the diluted egg yolk are selectively complexed with β-cyclodextrin, the complexed β-cyclodextrin is separated from the diluted egg yolk, water contained in the diluted egg yolk is removed to yield an egg yolk product with a reduced cholesterol content, and residual β-cyclodextrin present in the egg yolk product is enzymatically decomposed, the improvement which comprises recovering the β-cyclodextrin from the complexed β-cyclodextrin by treatment thereof with water, with an alcohol or with a mixture of water and an alcohol, and recycling the recovered β-cyclodextrin into the process for further selectively complexing cholesterol and cholesterol esters contained in diluted egg yolk.

17. The method of claim 16, wherein the egg yolk is diluted with 5 to 20% by weight of sodium chloride solution.

18. The method of claim 16, wherein the egg yolk is diluted with 1 to 15% by weight of an ammonium bicarbonate solution.

19. The method of claim 16, wherein the salt added for dilution of the egg yolk is removed after separation of the complexed β-cyclodextrin from the egg yolk.

20. The method of claim 19, wherein ammonium bicarbonate is removed from the egg yolk by evaporation at 40° to 80° C. in a vacuum.

21. The method of claim 20, wherein ammonium bicarbonate is removed by evaporation at a temperature of 55° to 70° C. in a vacuum.

22. The method of claim 19, wherein sodium chloride is separated from the diluted egg yolk by cross-flow ultrafiltration and electrodialysis.

23. The method of claim 16, wherein water is removed from the diluted egg yolk by vacuum distillation.

24. The method of claim 16, wherein residual β-cyclodextrin present in the egg yolk product is enzymatically decomposed with domestic hog pancreatic amylase or an α-amylase formed by a microorganism selected from the group consisting of *Aspergillus niger, Aspergillus oryzae, Bacillus polymyxa, Bacillus coagulans* and Flavobacterium.

25. The method of claim 24, wherein the β-cyclodextrin is enzymatically decomposed with 10 to 500 FAU per gram of β-cyclodextrin to be decomposed.

26. The method of claim 16, wherein the residual β-cyclodextrin present in the egg yolk product is enzymatically decomposed with a CTGase derived from or formed by a bacteria selected from the group consisting of Bacillus, Klebsiella, Micrococcus and alkalophilic bacteria.

27. The method of claim 16, wherein the β-cyclodextrin is enzymatically decomposed with 0.5 to 20 U per gram of β-cyclodextrin to be decomposed.

28. The method of claim 16, wherein the enzymatic decomposition of β-cyclodextrin is carried out at a temperature of 5° to 65° C.

* * * * *